(12) United States Patent
Wilson (10) Patent No.: US 7,775,211 B2
(45) Date of Patent: Aug. 17, 2010

(54) SNORING TREATMENT AND ASSOCIATED APPARATUS, SYSTEM AND METHOD

(76) Inventor: John K. Wilson, 310 Hurbutt St., Wilton, CT (US) 06897

( * ) Notice: Subject to any disclaimer, the term of this patent is extended or adjusted under 35 U.S.C. 154(b) by 126 days.

(21) Appl. No.: 11/512,542

(22) Filed: Aug. 30, 2006

(65) Prior Publication Data

US 2008/0053460 A1     Mar. 6, 2008

(51) Int. Cl.
| | |
|---|---|
| A61F 5/37 | (2006.01) |
| A61F 13/00 | (2006.01) |
| A61M 15/00 | (2006.01) |
| A61M 16/00 | (2006.01) |
| G09B 15/06 | (2006.01) |
| A63B 23/03 | (2006.01) |
| A63B 23/18 | (2006.01) |
| A61M 5/315 | (2006.01) |

(52) U.S. Cl. .................. 128/848; 128/846; 128/200.11; 128/200.22; 128/200.24; 128/205.23; 604/222; 482/11; 482/13; 84/465

(58) Field of Classification Search ................ 128/848, 128/857, 859–861, 200.11, 200.12, 200.22, 128/200.24, 205.23, 205.24, 203.23; 604/58, 604/239, 222; 482/11–13; 84/465
See application file for complete search history.

(56) References Cited

U.S. PATENT DOCUMENTS

| | | | | | |
|---|---|---|---|---|---|
| 4,648,393 | A | * | 3/1987 | Landis et al. | 128/200.23 |
| 4,940,051 | A | * | 7/1990 | Lankinen | 128/200.18 |
| 5,447,150 | A | * | 9/1995 | Bacon | 128/200.14 |
| 5,482,030 | A | * | 1/1996 | Klein | 128/200.23 |
| 6,125,844 | A | * | 10/2000 | Samiotes | 128/200.23 |
| 6,328,037 | B1 | * | 12/2001 | Scarrott et al. | 128/205.23 |
| 6,336,453 | B1 | * | 1/2002 | Scarrott et al. | 128/200.23 |
| 6,418,925 | B1 | * | 7/2002 | Genova et al. | 128/200.14 |
| 6,435,177 | B1 | * | 8/2002 | Schmidt et al. | 128/200.23 |
| 6,557,549 | B2 | * | 5/2003 | Schmidt et al. | 128/200.24 |
| 6,615,827 | B2 | * | 9/2003 | Greenwood et al. | 128/200.23 |
| 6,761,161 | B2 | * | 7/2004 | Scarrott et al. | 128/200.14 |
| 6,848,443 | B2 | * | 2/2005 | Schmidt et al. | 128/200.23 |
| 6,904,908 | B2 | * | 6/2005 | Bruce et al. | 128/200.23 |

(Continued)

OTHER PUBLICATIONS

Letter dated May 20, 2008, from Carl Rohde to John K. Wilson (3 pages).

(Continued)

*Primary Examiner*—Patricia M Bianco
*Assistant Examiner*—Brandon Jackson
(74) *Attorney, Agent, or Firm*—McCarter & English, LLP (57) ABSTRACT

The disclosed apparatus, systems and methods are effective in treating snoring behavior. Exemplary embodiments of the disclosed treatment apparatus include a mouthpiece, a first chamber in communication with the mouthpiece, and a displaceable member mounted with respect to the first chamber for applying a resistive force as gas is withdrawn from the first chamber. A second, substantially airtight chamber is generally defined on the opposite side of the displaceable member. The evacuation force required to deflect, deform or otherwise is increased due to the force required to displace the displaceable member positioned within the disclosed treatment apparatus. In exemplary embodiments of the disclosed apparatus, the displaceable member may take the form of a flexible membrane, piston or diaphragm that is mounted with respect to the inner wall of the first chamber or the second chamber. Use of the treatment apparatus is effective in reducing and/or eliminating snoring behavior for extended periods.

17 Claims, 6 Drawing Sheets

U.S. PATENT DOCUMENTS

| | | | |
|---|---|---|---|
| 6,953,039 B2 * | 10/2005 | Scarrott et al. | 128/200.14 |
| 7,201,164 B2 * | 4/2007 | Grychowski et al. | 128/200.23 |
| 7,201,165 B2 * | 4/2007 | Bruce et al. | 128/200.23 |
| 7,219,664 B2 * | 5/2007 | Ruckdeschel et al. | 128/200.14 |
| 2005/0011515 A1 * | 1/2005 | Lee et al. | 128/200.23 |
| 2006/0150971 A1 * | 7/2006 | Lee et al. | 128/203.15 |
| 2007/0277818 A1 | 12/2007 | Chen | |
| 2008/0066743 A1 * | 3/2008 | Grychowski et al. | 128/200.23 |

OTHER PUBLICATIONS

Letter dated Jun. 17, 2008, from Thomas R. Goots, Esq., to Mr. John K. Wilson (7 pages with Exhibits 1 and 2).

* cited by examiner

SNORING TREATMENT AND ASSOCIATED APPARATUS, SYSTEM AND METHOD

BACKGROUND

1. Technical Field

The present disclosure is directed to apparatus, systems and methods for snoring treatment and, more particularly, to an apparatus and treatment regimen that provides relief from snoring through utilization of a therapeutic device that ameliorates, in whole or in part, the condition.

2. Background Art

Approximately one third of the U.S. population, more than 80 million people, is reported to snore on a regular basis (Mayo Clinic). Snoring deprives both the individual who is snoring and any sleeping companions of sleep. Indeed, the Mayo Clinic reports that each of the noted individuals loses one hour of sleep per night due to such snoring behavior, with corresponding negative impacts on health and quality of life. More ominously, as many as twenty four percent (24%) of Americans are reported to suffer from sleep-disordered breathing (*Scientific American*, Jun. 6, 2005). Individuals suffering from obstructive sleep apnea have been found to stop breathing for up to fifteen (15) seconds with a remarkable frequency, e.g., hundreds of times per night. This condition increases the risk and/or incidence of high blood pressure, heart attack and stroke. According to the New England Journal of Medicine (Mar. 24, 2005), individuals suffering from obstructive sleep apnea are three (3) times as likely to die from a heart attack during the night. In addition, snoring generally increases in direct relation to age and weight, demographics that are evidencing significant increases in today's population.

Available treatment options for snoring generally fall into three categories: (1) highly invasive surgery (e.g., laser-assisted uvula palatoplasty (LAUP), and radio frequency surgical ablation (RFTA)), (2) relatively invasive, uncomfortable consumer devices (e.g., masks) with unproven effectiveness, and (3) over-the-counter remedies (e.g., nasal strips and throat sprays) with limited effectiveness. In view of the significant implications associated with snoring that remains untreated, effective treatment systems, methods and modalities are needed. In particular, effective treatment systems that are easy-to-use, non-invasive and with proven efficacy are needed.

The apparatus, systems and methods of the present disclosure address such needs, serving to reduce and/or eliminate snoring through non-invasive and easy-to-use treatment regimens, as will be apparent from the description which follows.

SUMMARY

An advantageous apparatus, system and method is provided for snoring treatment and reducing/eliminating the incidence of snoring by a user of the apparatus, system and/or method. According to exemplary embodiments hereof, the apparatus includes a mouthpiece, a first chamber in communication with the mouthpiece, and a displaceable member mounted with respect to the first chamber for applying a resistive force as gas is withdrawn from the first chamber. A second chamber is advantageously defined on the opposite side of the displaceable member, such second chamber defining a substantially airtight region. Based on the positioning of the displaceable member between the first and second chambers, the evacuation force required to deflect, deform or otherwise displace the displaceable member is increased.

In exemplary embodiments of the disclosed apparatus, the displaceable member may take the form of a flexible membrane, piston or diaphragm that is mounted with respect to the inner wall of the first chamber or the second chamber. In either case, the displaceable member responds to a user's attempted withdrawal of air from the first chamber, i.e., by sucking air through the mouthpiece, by deflecting, deforming or otherwise displacing toward the mouthpiece. The resistance experienced by the user generally increases as air is withdrawn/evacuated from the first chamber based on at least one of the following factors: (1) increased resistance offered by the displaceable member as it is asked to deflect, deform or otherwise displace to a greater extent, and/or (2) the resistance of the air within the substantially airtight second region to expanding into the additional volume defined by the deflection, deformation or other displacement of the displaceable member toward the mouthpiece.

An indicator mechanism may be mounted with respect to the displaceable member to provide a visually perceptible indication of the user's interaction with the disclosed apparatus, e.g., the degree to which the displaceable member is displaced toward the mouthpiece based on the user's interaction therewith. In an exemplary embodiment, the indicator mechanism includes a linkage assembly that is fixed with respect to the displaceable member and that translates travel of the displaceable member relative to the first/second chambers into a visually perceptible indication. Thus, a sealed slot or window may be provided in a wall of the second chamber through which an indicator may be visible, such indicator traveling relative to the slot/window based upon and in response to travel of the displaceable member relative to the first/second chambers.

The present disclosure further provides an advantageous treatment regimen for reducing and/or eliminating a user's snoring. According to exemplary embodiments of the disclosed treatment regimen, an individual is provided with an apparatus/device that includes a mouthpiece, a first chamber in communication with the mouthpiece, and a displaceable member mounted with respect to the first chamber for applying a resistive force with respect to the flow of gas from the first chamber, and (ii) withdrawing air from the first chamber through the mouthpiece against the resistance applied by the displaceable member. To gain clinically significant results from the disclosed method, the user is generally required to perform the noted "air withdrawal" step several times prior to retiring to bed. Between each repetition, the displaceable member advantageously and automatically returns to its initial rest position in preparation for the next repetition. In an exemplary embodiment of the disclosed treatment regimen, the user performs the air withdrawal step for a period of between one minute and fifteen minutes. Generally, favorable results may be expected when the treatment regimen is performed within one hour of the individual retiring to bed.

While not desiring to be limited to a particular clinical and/or anatomical explanation as to the reasons for the effectiveness of the disclosed snoring treatment regimen, it is believed that the advantageous snoring reduction/elimination is effectuated through the lifting of a user's palette based on use of the disclosed apparatus. Indeed, it is believed that lifting of a user's palette to a requisite degree is effective in reducing/eliminating a user's snoring, and that repeated treatments over a period of time may be effective in permanently or semi-permanently lifting a palette such that snoring is reduced/eliminated for an extended period, e.g., for a period of days, weeks, months, etc. Preliminary tests with the disclosed apparatus and associated treatment regimen have demonstrated snoring-free sleep patterns for extended periods, e.g., about six hours.

Additional advantageous features, functions and benefits of the disclosed apparatus, system and treatment methods will be apparent from the detailed description which follows, particularly when read in conjunction with the appended figures.

BRIEF DESCRIPTION OF THE FIGURES

To assist those of ordinary skill in the art in making and using the disclosed apparatus/systems, reference is made to the accompanying figures, wherein.

DESCRIPTION OF EXEMPLARY EMBODIMENT(S)

The disclosed apparatus, systems and methods are effective in snoring treatment. As described in greater detail below, exemplary embodiments of the disclosed treatment apparatus include a mouthpiece, a first chamber in communication with the mouthpiece, and a displaceable member mounted with respect to the first chamber for applying a resistive force as gas is withdrawn from the first chamber. A second, substantially airtight chamber is generally defined on the opposite side of the displaceable member. The evacuation force required to deflect, deform or otherwise displace the displaceable member is increased due to the force required to displace the displaceable member positioned within the disclosed treatment apparatus. In exemplary embodiments of the disclosed apparatus, the displaceable member may take the form of a flexible membrane, piston or diaphragm that is mounted with respect to the inner wall of the first chamber or the second chamber.

Figure 1:
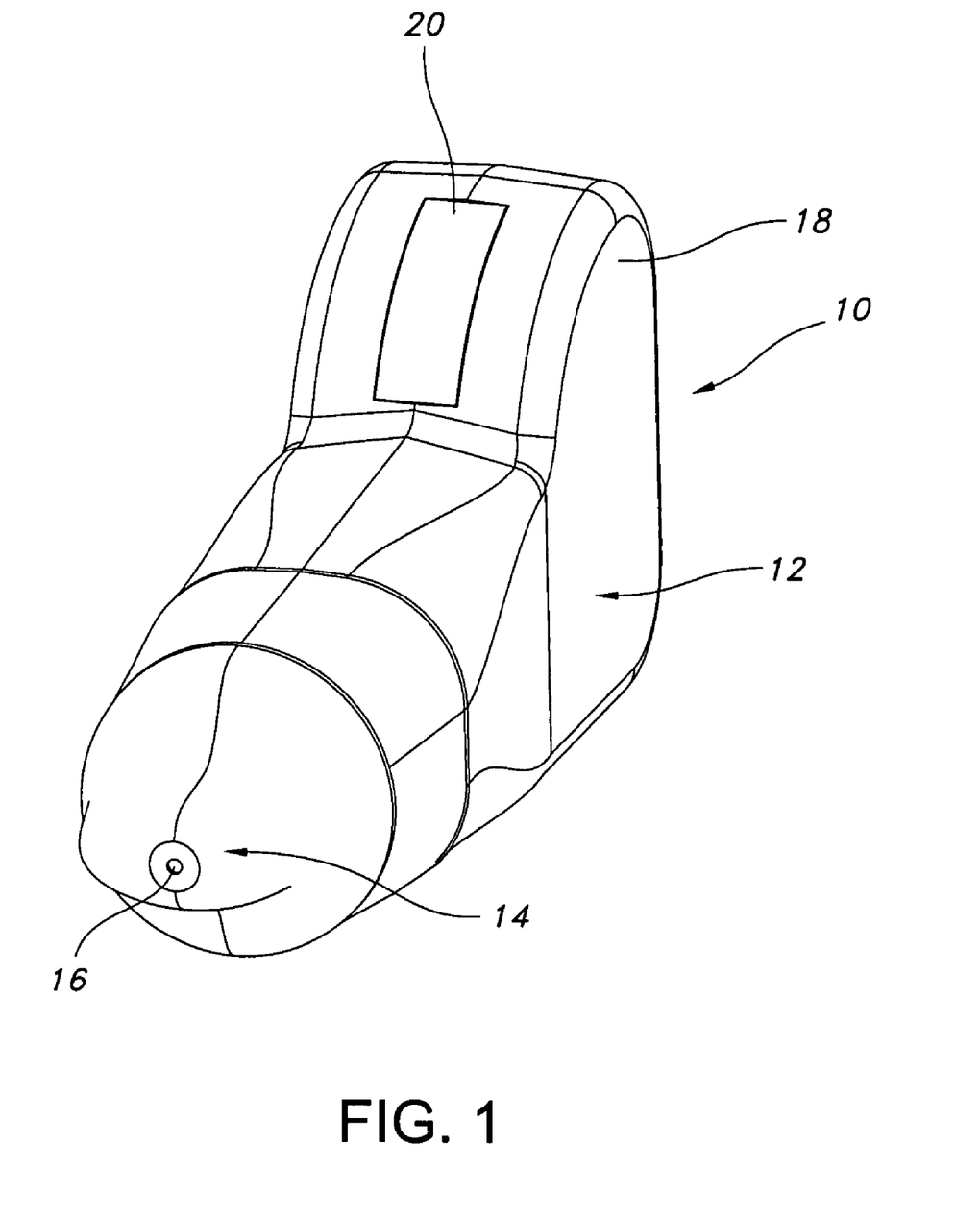
FIG. 1 is a front view of an exemplary treatment apparatus according to the present disclosure.

Turning to FIG. 1, an exemplary treatment apparatus 10 is depicted. Treatment apparatus 10 includes an outer housing 12 and a mouthpiece 14. The mouthpiece 14 is generally configured and dimensioned to be comfortably positioned within a user's mouth. Chamfered and/or radiused surfaces may be provided to enhance user interaction therewith. An opening 16 is formed in mouthpiece 14 to permit air passage therethrough. As used herein, the term "air" includes both respirated and non-respirated air. While the overall size/dimensional characteristics of outer housing 12 are not critical, the outer housing is generally of sufficient size to define internal chambers that are effective to achieve the snoring treatment effects described herein. According to exemplary embodiments of the present disclosure, the outer housing 12 is also sized so as to be easily held/handled by a user of the treatment apparatus. Exemplary dimensions of an illustrative treatment apparatus include a length (from mouthpiece to end of second chamber) of about 7 inches, a width of about 1.5 to 2 inches, and a height in the bulbous region 18 (described below) of about 3 inches. Alternative geometries may be employed without departing from the spirit or scope of the present disclosure.

With further reference to FIG. 1, outer housing 12 defines a distal bulbous region 18. A sealed slot or window 20 is formed on the face of bulbous region 18. Of note, due to the upward expanse of bulbous region 18 relative to mouthpiece 14, slot/window 20 is substantially in visual alignment with a user's eyes when he/she positions the mouthpiece 14 in his/her mouth. As described in greater detail herein below, slot/window 20 cooperates with a visual indicator mechanism that reflects the user's interaction with the treatment apparatus.

Figure 2:
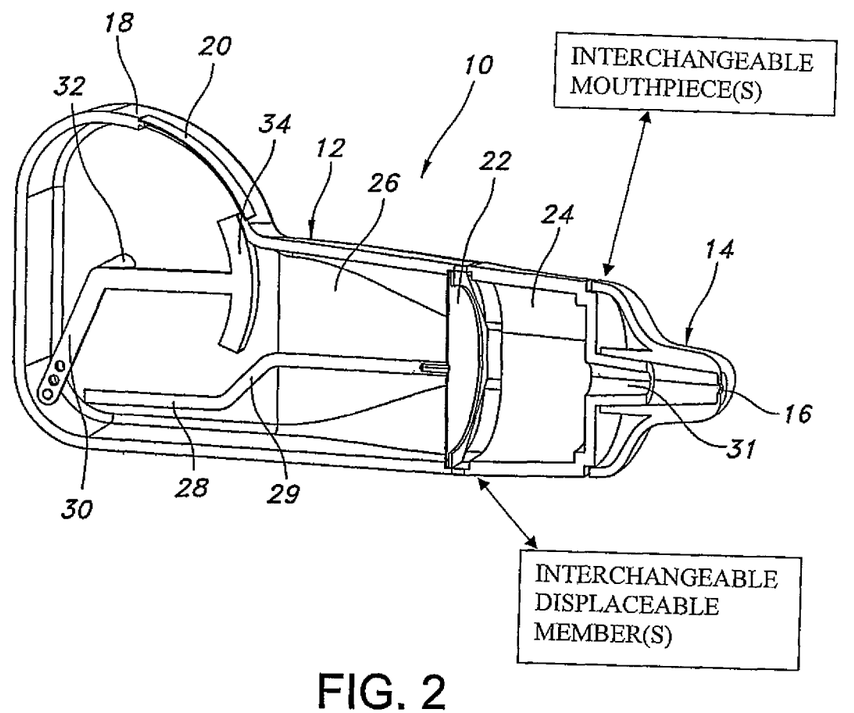
FIG. 2 is a cross-sectional view of the exemplary treatment apparatus of FIG. 1.

Turning to FIG. 2, a cross-sectional view of treatment apparatus 10 is provided. A displaceable member 22 is positioned within and mounted with respect to outer housing 12. In the exemplary embodiment of FIG. 2, displaceable member 22 takes the form of an elastic or flexible membrane fabricated from a rubber or rubber-like material. However, the displaceable member 22 may take various alternative forms, e.g., a piston assembly that is adapted to translate relative to the outer housing 12 in response to forces as described herein. Thus, the present disclosure expressly encompasses alternative displaceable member designs, as will be readily apparent to persons skilled in the art based on the disclosure provided herein.

A first chamber 24 is defined on the mouthpiece side of displaceable member 22 and a second chamber 26 is formed on the opposite side thereof. The second chamber 26 extends into bulbous region 18 and is airtight, i.e., air captured therewithin cannot escape from outer housing 12. First chamber 24 communicates through mouthpiece 14 and opening 16 to the external atmosphere. Of note, a channel 31 is formed within mouthpiece 14 to funnel/guide air between opening 16 and first chamber 24. The channel 32 may take the form of a cylindrical extension positioned within mouthpiece 14.

A first linkage 28 is mounted with respect to displaceable member 22, e.g., through an adhesion technique. First linkage 28 is mounted with respect to a second linkage 30 (although in FIG. 2 the two linkages 28, 30 are separated for clarity purposes). First linkage 28 defines a jog 29 that facilitates operation of the disclosed linkage mechanism. Second linkage 28 defines an angled structure, typically an obtuse angle, and is pivotally mounted with respect to outer housing 12, e.g., with respect to a pair of mounting extensions 32 (only one mounting extension 32 is visible in the cross-sectional view of FIG. 2) that extend inwardly from opposed faces of the outer housing 12. An arcuate indicator surface 34 is formed or mounted to the end of second linkage 30. Indicator surface 34 is adapted to cooperate with sealed slot/window 20 formed in outer housing 12 to indicate travel/displacement of the displaceable member 22 relative to the outer housing 12.

Figure 3:
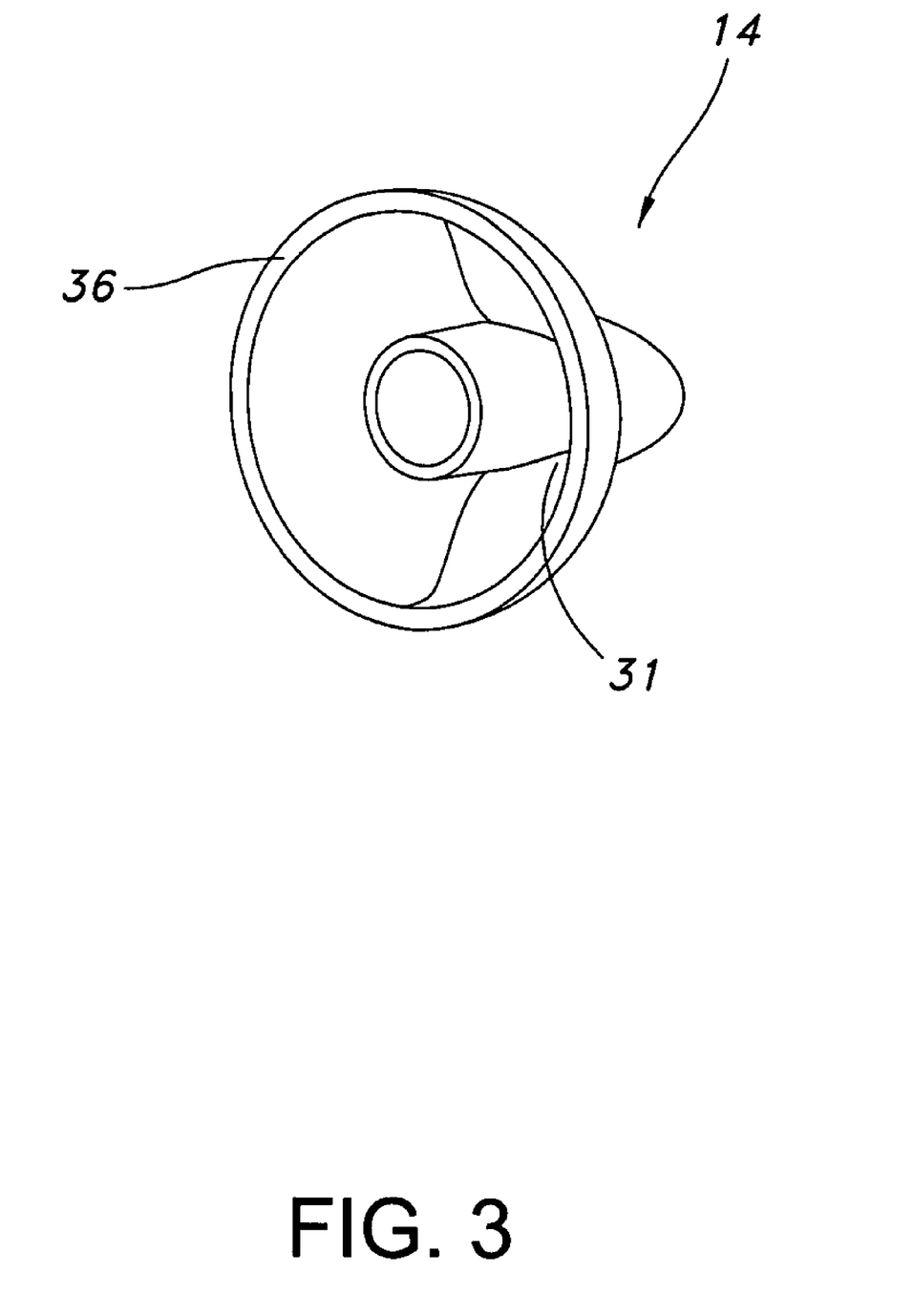
FIG. 3 is a view of an exemplary mouthpiece component according to the disclosed treatment apparatus.

Additional details of an exemplary mouthpiece 14 according to the disclosed exemplary treatment apparatus are depicted in FIG. 3. As shown therein, a cylindrical channel 31 is defined within mouthpiece 14 for guiding air to and from mouthpiece opening 16 (not visible). In the exemplary mouthpiece 14 depicted in FIG. 3, a substantially circular mounting face 36 is defined thereby. Mounting face 36 facilitates assembly of mouthpiece 14 to the other component(s) associated with the disclosed treatment apparatus 10. Thus, for example, mouthpiece 14 may be designed to be detachable/replaceable from the other component(s), thereby permitting multiple users to have personal mouthpieces for use therewith. In such circumstances, a "quick-connect" feature may be incorporated into/onto mouthpiece 14, e.g., a screw thread, snap-lock, bayonet lock or the like.

Figure 4:
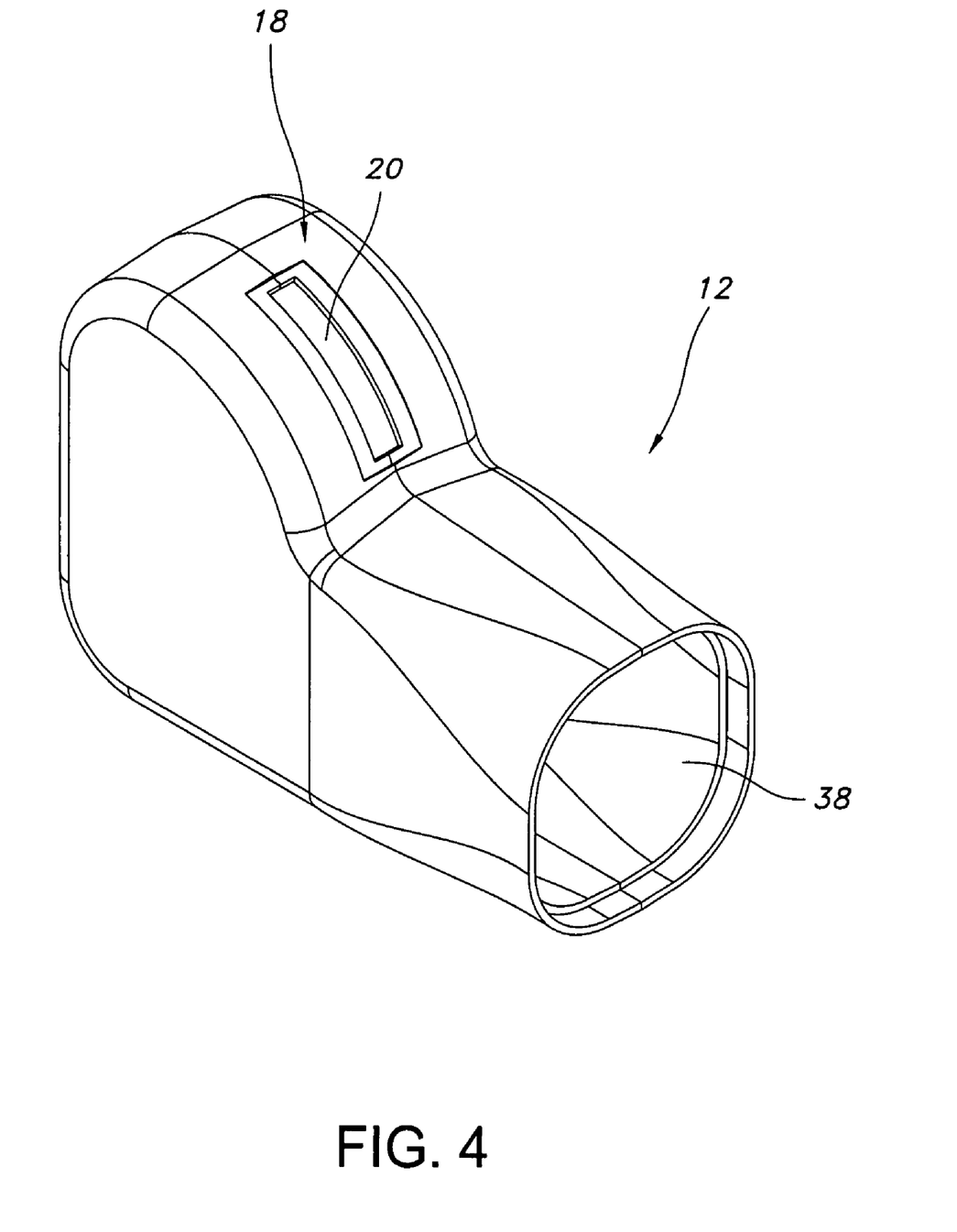
FIG. 4 is a plan view of an exemplary outer housing component according to an exemplary embodiment of the present disclosure.
Figure 5:
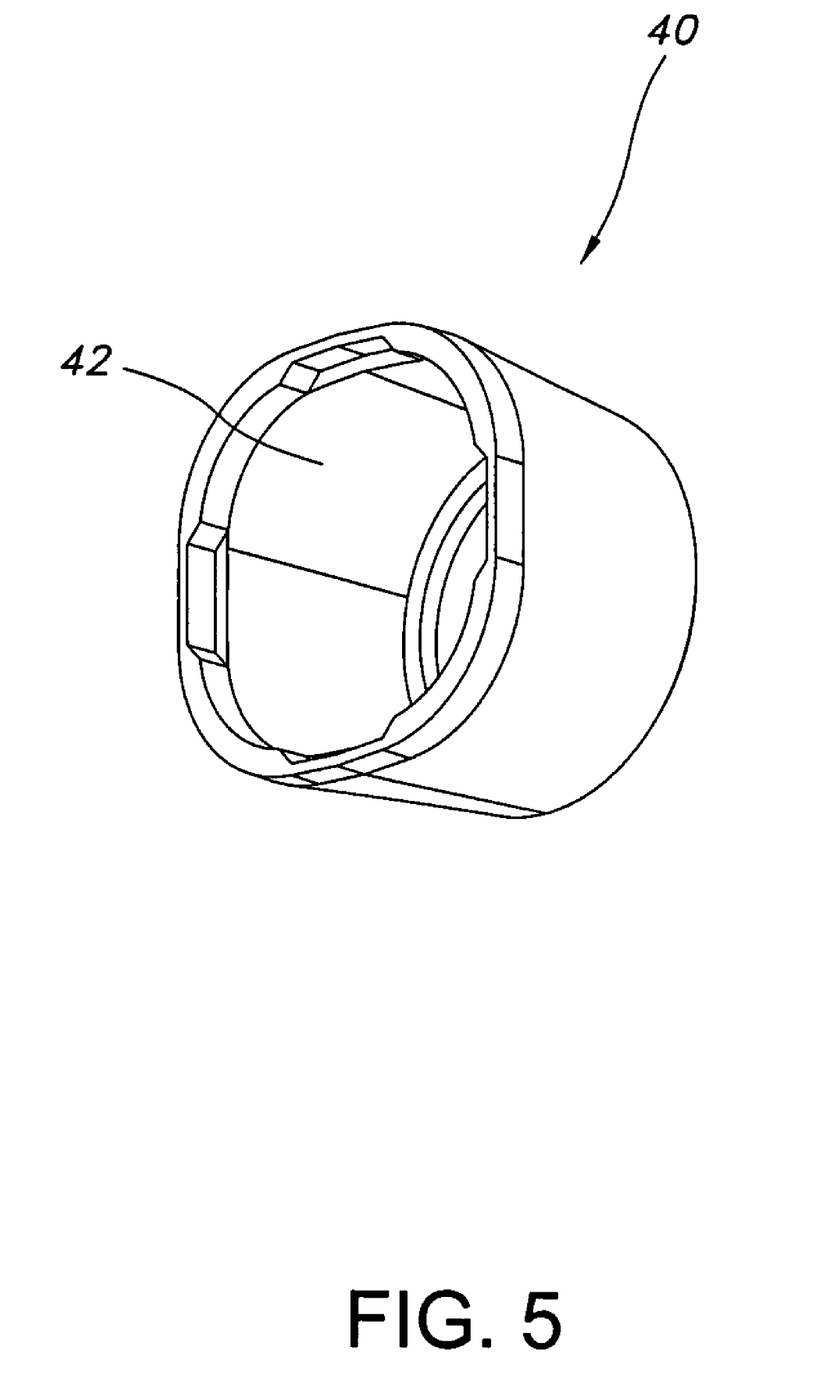
FIG. 5 is a plan view of an intermediate housing component that is adapted to receive a displaceable member according to the present disclosure.

FIG. 4 provides a further view of a portion of an exemplary outer housing 12 according to the present disclosure. An opening 38 is defined in a forward region thereof for cooperation with an intermediate component 40, as shown in FIG. 5. The displaceable member 22 is typically mounted with respect to the opening 42 defined in intermediate component 40, although alternative mounting designs may be employed without departing from the spirit or scope of the present disclosure. Once a displaceable member 22 is mounted with respect to the intermediate component 40, the intermediate component and the portion of the outer housing 12 shown in FIG. 4 (with the linkage mechanism extending into the internal cavity of such outer housing portion in the manner shown in FIG. 2), the mouthpiece 14 may be secured with respect thereto, thereby forming a complete treatment apparatus assembly.

In typical use of treatment apparatus 10, the displaceable member 22 responds to a user's attempted withdrawal of air from the first chamber 24, i.e., by sucking air through the opening 16 in the mouthpiece 12, by deflecting, deforming or otherwise displacing toward the mouthpiece 14. The resistance experienced by the user generally increases as air is withdrawn/evacuated from the first chamber 24 based on at least one of the following factors: (1) increased resistance offered by the displaceable member 22 as it is asked to deflect, deform or other displace to a greater extent, and/or (2) the resistance of the air within the substantially airtight second chamber 26 to expanding into the additional volume defined by the deflection, deformation or other displacement of the displaceable member 22 toward the mouthpiece 14.

An indicator mechanism is defined by the linkage mechanism described herein, i.e., linkages 28, 30 and indicator surface 34 may be mounted with respect to the displaceable member 22 to provide a visually perceptible indication of the user's interaction with the disclosed treatment apparatus 10, e.g., the degree to which the displaceable member 22 is displaced toward the mouthpiece 14 based on the user's interaction therewith. The linkage assembly is fixed with respect to the displaceable member 22 and translates travel of the displaceable member 22 relative to the first/second chambers 24, 26 into a visually perceptible indication. Thus, the sealed slot or window 20 permits viewing of indicator surface 34 therethrough, such indicator surface 34 traveling relative to the slot/window 20 based upon and in response to travel of the displaceable member 22 relative to the first/second chambers 24, 26.

An advantageous treatment regimen for reducing and/or eliminating a user's snoring is provided through use of the disclosed treatment apparatus. According to exemplary embodiments of the disclosed treatment regimen, an individual is provided with an apparatus/device that includes a mouthpiece, a first chamber in communication with the mouthpiece, and a displaceable member mounted with respect to the first chamber for applying a resistive force with respect to the flow of gas from the first chamber, and such user withdraws air from the first chamber through the mouthpiece against the resistance applied by the displaceable member. To gain clinically significant results from the disclosed method, the user is generally required to perform the noted "air withdrawal" step several times prior to retiring to bed. Between each repetition, the displaceable member advantageously and automatically returns to its initial rest position in preparation for the next repetition. In an exemplary embodiment of the disclosed treatment regimen, the user performs the air withdrawal step for a period of between one minute and fifteen minutes. Generally, favorable results may be expected when the treatment regimen is performed within one hour of the individual retiring to bed.

Figure 6:
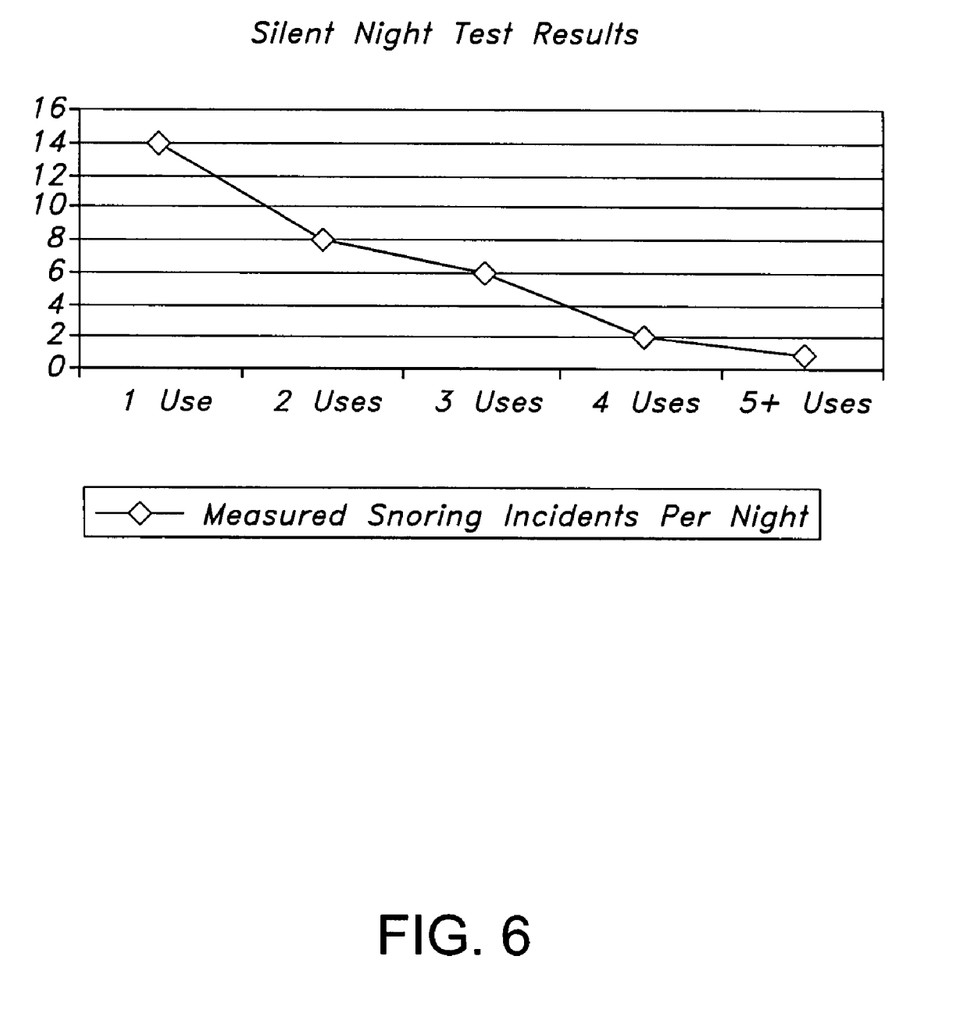
FIG. 6 is a plot of improved snoring behavior achieved through use of the disclosed treatment apparatus.

Indeed, FIG. 6 demonstrates extremely favorable, preliminary results achieved through use of the disclosed treatment apparatus on repeated occasions, with snoring incidents (as measured by a sound-actuated recording device) decreasing significantly. In the preliminary results set forth in FIG. 6, snoring incidents were reduced to only fourteen (14) based on one use of the disclosed treatment apparatus, and fell to less than two (2) snoring incidents after five (5) uses.

While not being limited to a particular clinical and/or anatomical explanation in support of the disclosed treatment regimen, it is believed that the advantageous reduction/elimination of snoring is effectuated through the lifting of the user's palette. Indeed, it is believed that lifting of a user's palette is effective to reduce/eliminate snoring in a user, and that repeated treatments over a period of time may be effective in permanently or semi-permanently lifting a palette such that snoring is reduced/eliminated for an extended period, e.g., days, weeks, months, etc.

Although the present disclosure has been described with reference to exemplary embodiments of the advantageous treatment apparatus, system and treatment regimen, the present disclosure is not limited by such exemplary embodiments. Rather, such exemplary embodiments are merely illustrative of potential implementations of the disclosed treatment apparatus, system and method. Indeed, the present disclosure expressly encompasses enhancements, modifications and/or variations on the disclosed embodiments that do not depart from either the spirit or scope of the present disclosure.

The invention claimed is:

1. A method for snoring treatment, comprising:
   a. providing a treatment apparatus that includes (i) a housing defining a first chamber, (ii) a mouthpiece in flow communication with the first chamber, said mouthpiece defining the sole flow path into and out of the first chamber, and (iii) a displaceable member mounted with respect to the housing and defining an impermeable boundary of said first chamber, said displaceable member functioning to apply a resistive force with respect to outward flow of gas from the first chamber through the mouthpiece without creating a flow passage that would permit gas to flow to or from the first chamber in any way other than through the mouthpiece;
   b. withdrawing air from the first chamber through the mouthpiece against the resistive force applied by the displaceable member.

2. A method according to claim 1, wherein the displaceable member provides resistance to withdrawal of air through the mouthpiece and automatically resumes a non-displaced orientation when air withdrawal is discontinued and air reenters the first chamber through the mouthpiece.

3. A method according to claim 2, wherein the resistance is based on at least one of the following factors: (i) increased resistance offered by deflection, deformation or displacement of the displaceable member; and (ii) resistance of air within a substantially airtight second region to expanding into the additional volume defined by the deflection, deformation or displacement of the displaceable member toward the mouthpiece.

4. A method according to claim 1, wherein air is repeatedly withdrawn from the first chamber by a user prior to retiring to bed.

5. A method according to claim 4, wherein air is repeatedly withdrawn from the first chamber for a period of one minute to fifteen minutes.

6. A method according to claim 1, wherein the treatment regimen is undertaken for a period of time so as to be effective to ameliorate an individual's snoring.

7. A method according to claim 6, wherein the treatment regimen is undertaken for a period of time so as to be effective to prevent snoring for a period of up to six hours.

8. A method according to claim 1, wherein the treatment apparatus further includes a second chamber defined opposite the first chamber, the second chamber being substantially airtight and being sealed on at least one side by the displaceable member.

9. A method according to claim 1, wherein the displaceable member is selected from a flexible membrane, a piston, a diaphragm, and combinations thereof.

10. An apparatus for snoring treatment, comprising:
  a. a housing defining a first chamber,
  b. a mouthpiece in flow communication with the first chamber, said mouthpiece defining the sole flow path into and out of the first chamber, and
  c. a displaceable member mounted with respect to the housing and defining an impermeable boundary of said first chamber, said displaceable member functioning to apply a resistive force with respect to outward flow of gas from the first chamber through the mouthpiece without creating a flow passage that would permit gas to flow to or from the first chamber in any way other than through the mouthpiece.

11. An apparatus according to claim 10, wherein the displaceable member provides resistance to withdrawal of air through the mouthpiece and automatically resumes a non-displaced orientation when air withdrawal is discontinued and air reenters the first chamber through the mouthpiece.

12. An apparatus according to claim 11, wherein the resistance is based on at least one of the following factors: (i) increased resistance offered by deflection, deformation or displacement of the displaceable member; and (ii) resistance of air within a substantially airtight second region to expanding into the additional volume defined by the deflection, deformation or displacement of the displaceable member toward the mouthpiece.

13. An apparatus according to claim 10, further including a plurality of displaceable members that are interchangeably received with respect to the first chamber.

14. An apparatus according to claim 13, wherein the plurality of displaceable members are adapted to provide different resistance levels.

15. An apparatus according to claim 10, further including a second chamber defined opposite the first chamber, the second chamber being substantially airtight and being sealed on at least one side by the displaceable member.

16. An apparatus according to claim 10, wherein the displaceable member is selected from a flexible membrane, a piston, a diaphragm, and combinations thereof.

17. An apparatus according to claim 10, further including a plurality of mouthpieces that are interchangeably received by the first chamber.

* * * * *